United States Patent [19]
VonBargen

[11] Patent Number: 5,426,713
[45] Date of Patent: Jun. 20, 1995

[54] FIBER OPTIC PROBE WITH TRUNCATED CONE WINDOW BLOCK FOR INFRARED SPECTRAL ANALYSIS INSTRUMENT

[75] Inventor: Kenneth P. VonBargen, Berwyn Heights, Md.

[73] Assignee: NIRSystems Incorporated, Silver Spring, Md.

[21] Appl. No.: 149,949

[22] Filed: Nov. 10, 1993

[51] Int. Cl.[6] .................... G02B 600; G01N 21/31; G01N 21/47
[52] U.S. Cl. .................................... 385/15; 356/446; 250/227.29
[58] Field of Search ................. 385/15, 120, 115, 902; 356/446, 445; 250/227.29, 576

[56] References Cited

U.S. PATENT DOCUMENTS

| | | | |
|---|---|---|---|
| 3,973,849 | 8/1976 | Jackson et al. | 356/320 |
| 4,184,175 | 1/1980 | Mullane, Jr. | 250/562 |
| 4,643,573 | 2/1987 | McLachlan et al. | 356/338 |
| 4,707,134 | 11/1987 | McLachlan et al. | 356/342 |
| 4,768,879 | 9/1988 | McLachlan et al. | 356/301 |
| 4,782,226 | 11/1988 | Jeffries et al. | 250/227.11 |
| 4,978,863 | 12/1990 | Lyons et al. | 250/574 |
| 5,078,493 | 1/1992 | Evens et al. | 250/343 |
| 5,140,169 | 8/1992 | Evens et al. | 250/576 |
| 5,246,109 | 9/1993 | Markle | 385/56 |
| 5,304,173 | 4/1994 | Kittrell et al. | 606/15 |

*Primary Examiner*—Akm E. Ullah
*Attorney, Agent, or Firm*—Lane, Aitken & McCann

[57] ABSTRACT

In a fiber optic probe for an infrared analysis instrument, a window block made of sapphire is provided having an inner face in the shape of a truncated cone. A fiber optic cable has its distal end adjacent to the inner face of the window block and the optic fibers in the distal end are segregated into transmitting fibers adjacent to said conical section of the inner face of the window block and receiving fibers abutting the central circular portion formed by the truncated cone shape of the inner face. A cylindrical separator separates the receiving and transmitting fibers at the distal end of the fiber optic cable.

12 Claims, 2 Drawing Sheets

FIBER OPTIC PROBE WITH TRUNCATED CONE WINDOW BLOCK FOR INFRARED SPECTRAL ANALYSIS INSTRUMENT

This invention relates to near infrared spectral analysis instruments and, more particularly, to a near infrared spectral analysis instrument with an improved fiber optic probe to transmit and receive light from a sample.

BACKGROUND OF THE INVENTION

A powerful technology for analyzing matter involves measuring the reflectance from or the transmission through the matter to be analyzed at a narrow band wavelength in the near infrared region known as NIR. To carry out such analysis, the matter is irradiated with NIR light and the amount of light transmitted through or reflected from the matter at narrow band wavelengths is measured and analyzed. Instruments for making such analyses are disclosed in U.S. Pat. No. 4,969,739 to Phillip A. McGee, U.S. Pat. Nos. 4,264,205 and 4,285,596 to Issac J. Landa and U.S. Pat. No. 4,040,747 to Donald R. Webster. Frequently, such infrared analyzing instruments employ a fiber optic probe as a convenient technique to transmit the light from a near infrared source to the sample to be analyzed and to receive diffusely reflected light back from the sample and transmit the received light back to the instrument. A window is employed in the distal end of the probe between the transmitting fibers and the sample, which window must be transmissive to infrared light. Typically, the window is made of sapphire or quartz and has a relatively high index of refraction. The surfaces of the window, and particularly the outer surface of the window being a plane optical surface at which the index of refraction changes abruptly, has a tendency to specularly reflect light and it is important to prevent this specularly reflected light from being received by the receiving optical fibers in the fiber optic probe and transmit it back to the instrument as such specularly reflected light intertwines with the instrument capability of detecting the intensity diffusely reflected light from the sample.

U.S. Pat. No. 5,166,756, issued Nov. 24, 1992 to Phillip McGee et al., discloses a fiber optic probe which achieves elimination of spectral reflection by forming the outer face of a window block of the probe skewed at an angle to the axis of the probe. Pending U.S. application Ser. No. 07/931,783 discloses a probe with a two-piece window with a window block having a skewed internal face to prevent spectral reflection from being received.

SUMMARY OF THE INVENTION

The present invention provides an improved fiber optic probe structure which eliminates any spectrally reflected light from the interfaces of the distal window of the probe from reaching the optic fibers of the fiber optic probe without resorting to an outer window face which is skewed relative to the axis of the probe and also without resorting to a two-piece window.

In accordance with the present invention, the probe is provided with a window block which is preferably made of sapphire. The window block is provided with a planar outer face perpendicular to the axis of the probe and an inner face in the form of a truncated cone having a planar central circular section surrounded by a conical section. The optic fibers of the fiber optic cable connected with the probe terminate in a distal face at the inner face of the window block. The distal end of the fiber optic cable is coaxially divided into a central portion, which abuts against the central planar section of the inner face of the window block, and an outer section, which is positioned adjacent to, but spaced from, the conical section of the inner face of the window block. The two portions of the distal end of the fiber optic cable are separated by a cylindrical separator, which is aligned with the boundary between the central planar section of the inner face of the window block and the surrounding conical section of the interface of the window block.

In accordance with the preferred embodiment, the transmitting optic fibers, that is, the optic fibers which transmit light from the instrument to the window block, are segregated at the distal end of the fiber optic cable in the outer portion of the fiber optic cable surrounding the cylindrical divider and the receiving optic fibers, which receive diffusely reflected light back from the sample and transmit it to the instrument, are segregated at the distal end of the fiber optic cable within the cylindrical divider. The axes of the distal ends of the receiving fibers 17 are perpendicular to the planar central section 39 of the inner face of the window block 27. Light transmitted by the transmitting fibers, upon being emitted from the optic fibers, will pass through the conical section of the window block inner face and be refracted toward the center of the outer face of the window block thus intensifying the light transmitted to the center of the outer face of the window. Light specularly reflected within in the window block at the outer face of the window block will be reflected at an angle at the outer face to pass beyond the central planar section of the inner face of the window block so that this specularly reflected light will not be received by the receiving optic fibers in the central portion of the distal end of the fiber optic cable.

The arrangement of the optic fibers and the divider between the transmitting and receiving fibers ensures that no light transmitted from the transmitting fibers and reflected at the interface of the window block will reach the receiving optic fibers in the fiber optic cable. Accordingly, the index of refraction matching fluid typically required in the interface between the fiber optic cable and the window block can be eliminated. This matching fluid has a tendency to leak out or evaporate in high temperature applications and becomes a maintenance problem. Because the arrangement of the optic fibers in the distal end of the fiber optic cable, the receiving fibers will not receive any light reflected at reflected at the inner surface of the window block even though there is no matching fluid in this interface and even if a gap occurs between the end face of the optic fibers and the circular central section of the inner face of the window block.

DESCRIPTION OF A PREFERRED EMBODIMENT

Figure 1:
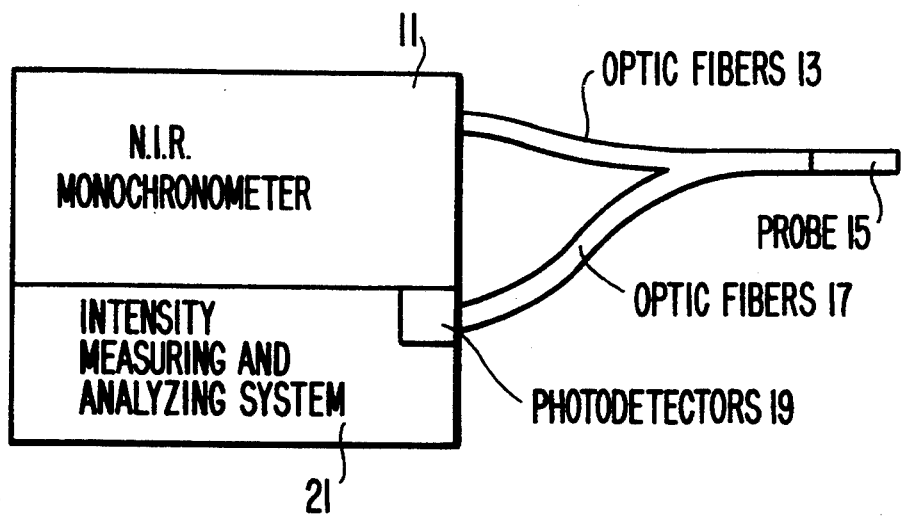
FIG. 1 schematically illustrates a spectral analysis instrument in which the improved fiber optic probe of the present invention is used.

As shown in FIG. 1, an NIR monochrometer 11 transmits narrow band infrared light through a flexible optic fibers 13 to a probe 15. The infrared monochrometer may be an instrument such as disclosed in U.S. Pat. No. 4,969,739, invented by Philip A. McGee et al. and assigned to the assignee of the present invention. The NIR monochrometer described in the above-identified patent comprises an oscillating grating which disperses light from a light source into its spectral components. As the grating oscillates, it scans the center wavelength of a narrow band of infrared light transmitted through an exit slit. The entrance ends of the optic fibers 13 are arranged in the shape of the exit slit of the monochrometer 11 and are positioned to receive the near infrared light transmitted through the exit slit of the near infrared monochrometer. Instead of using an oscillating grating, the narrow band wavelength could be provided by an interference filter or filters and the center wavelength scanned by tilting the filters. Alternatively, discrete narrow band wavelengths can be provided by light emitting diodes.

The optic fibers 13 are combined in a fiber optic cable with optic fibers 17, which are used to carry reflected light received by the probe 15 back to photodetectors 19. The photodetectors 19 convert the received light into an electrical signal having an amplitude corresponding to the intensity of the received light. The photodetectors 19 are part of an intensity measuring and analyzing system 21 which measures the amplitude of the output signal from the photodetectors thereby providing a measurement of the intensity of the light received by the photodetectors and reflected from a sample at the window 23. The amplitude values measured in this manner are then used to analyze the sample by the analyzing system, such as in the manner disclosed in the Webster U.S. Pat. No. 4,040,747.

Figure 2:
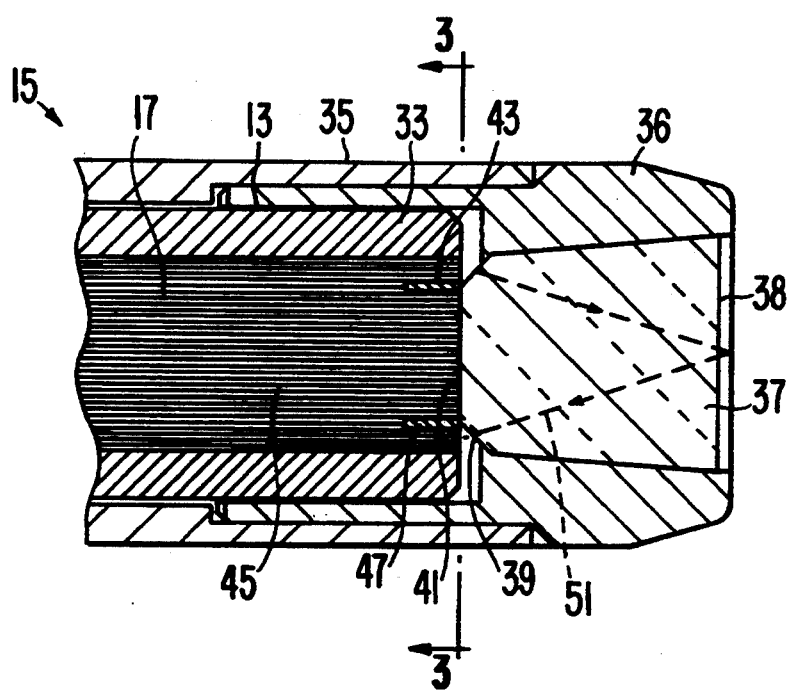
FIG. 2 is an axial section in elevation of a fiber optic probe in accordance with the present invention.
Figure 3:
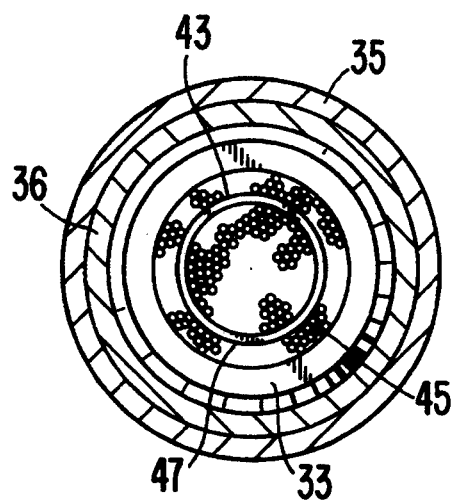
FIG. 3 is a cross-sectional view of the probe of the invention taken along the line 3—3 of FIG. 2.

In the probe 15 as shown in FIGS. 2 and 3, the optic fibers 13 and 17 of the fiber optic cable are enclosed in a sheath 33 which in turn is housed in a probe housing 35. A window mount 36 is fixed in the distal end of the housing 35 and a sapphire window block 37 is mounted in the window mount 36. The sapphire window block has a planar outer face 38 and an inner face in the form of a truncated cone having a conical outer section 39 and a circular central planar section 41. The distal ends of the optic fibers 13 and 17 are divided coaxially into an outer annular portion 43 and a cylindrical central portion 45. The annular portion 43 of the optic fibers is separated from the central portion 45 of the optic fibers by a coaxial cylindrical divider 47 at the distal end of the fiber optic cable. The distal ends of the optic fibers in the central portion 45 abut against the planar central end face 41 of the window block 37. The separator 47 is aligned with the circular boundary between the central planar section 41 and the conical section 39 of the inner face of the window block. The distal ends of the optic fibers in the outer annular portion 43 are separated from the conical surface 39 by a gap within the window mount 36.

In accordance with the preferred embodiment, the side walls of the window block 37 extending between the conical end face section 39 and the front face 38 are tapered or, in other words, are slightly conical to fit with correspondingly inner tapered walls of the window mount 36 and the window block 37 is press fit within the window mount 36 to form an airtight seal between the window block 38 and the window mount 36.

In the preferred embodiment of the invention, the optic fibers in the outer annular portion 43 consist of the transmitting optic fibers 13 which transmit light from the NIR monochrometer 11 and the optic fibers in the central cylindrical portion 45 consist of receiving optic fibers 17 which transmit received light from the probe 15 to the photodetectors 19.

The light transmitted through the optic fibers 13 and emitted from the distal ends of these fibers is transmitted through the gap between the distal ends of these fibers and the conical section 39 of the inner face of the window block 37 and passes through the conical section 39, which refracts the light toward the center of the outer face 38 of the window block 37, thus tending to focus the light in the center of the outer face of the window block. Some of the transmitted light will be specularly reflected at the outer face 38 back towards the fiber optic cable, as represented by the exemplary ray 51. The angle of refraction provided by the conical surface combined with the axial length of the window block are such that all of the specularly reflected light will be reflected at angles such that it will reach the inner face of the window block 37 outside of the cylindrical divider 47 so that none of the specularly reflected light will be received by the receiving optic fibers 17, which are segregated in the cylindrical central portion 45 of the distal end of the fiber optic cable. In this manner, light specularly reflected from the outer face 38 is prevented from being received by the receiving optic fibers 17 and reaching the photodetectors 19.

In accordance with a preferred specific embodiment, the angle of the conical surface relative to the axis of the probe is 45 degrees, the axial length of the probe from the planar central section 41 of the inner face of the window block to the outer face 38 is 0.344 inches and the diameter of the planar central section 41 is 0.177 inches in diameter. With these dimensions and employing a sapphire window block or a window block with a corresponding index of refraction, all of the light rays transmitted from the transmitting fibers 13, refracted at the conical section 39, and specularly reflected from the outer face 38 are reflected at an angle to reach the inner face of the window block 37 beyond the cylindrical divider 47.

The fiber optic probe of the present invention does not require index matching fluid between the window block and the fiber optic cable and, preferably, index matching fluid is not used. No index matching fluid is needed because of the coaxial segregation of the transmitting and receiving optic fibers at the distal end of the coaxial cable. With this arrangement, light transmitted from the transmitting fibers and specularly reflected at the inner face of the window block should not be received by the receiving fibers. This advantage of the probe is facilitated by use of the cylindrical separator 47 coinciding with the boundary between the conical interface section 39 and the circular interface section 41. The separator 47 assures that no light from a transmitting fiber will be specularly reflected from the inner face of the window block and be received by a receiving fiber.

In the preferred embodiment as described above, the transmitting fibers are located in the annular portion 43 at the distal end of the fiber optic cable and the receiving fibers are located in the cylindrical portion 45 at the distal end of the fiber optic cable. As an alternative, this arrangement could be reversed, in which case the effect of eliminating light specularly reflected from the outer face 38 would not be perfectly achieved. However, in such a modified probe, the coaxial segregation of the transmitting and receiving fibers in combination with the cylindrical separator, will prevent light reflected at the inner face of the probe from reaching the receiving fibers without the use of index of refraction matching fluid and the advantages of the elimination of this index of refraction matching fluid is obtained.

In the preferred embodiment as described above, the inner face of the window block is shaped in the form of a truncated cone. Other shapes in which one section or sections of the inner face are perpendicular to the optic fibers and the ether section or sections are at an angle to the first section could also be used, such as a truncated pyramid.

The above description is of preferred embodiments of the present invention and modification may be made thereto without departing from the spirit and scope of the invention, which is defined in the appended claims.

I claim:

1. A fiber optic probe comprising a fiber optic cable having optic fibers terminating is the distal end of said fiber optic cable, a transparent window block having an inner face positioned adjacent to said distal end of said fiber optic cable, said optic fibers being segregated into a first set having distal ends in a first portion of the distal end of said fiber optic cable and a second set having distal ends in a second portion of the distal end of said fiber optic cable, said inner face of said window block having a first planar section arranged perpendicularly to the distal ends of said fiber optics of said first set and a second section at an angle to said first section and positioned opposite to the distal end of the optic fibers of said second set, said window block having an outer face opposite said inner face arranged to transmit light transmitted through said window block from the optic fibers of one of said first and second sets.

2. A fiber optic probe as recited in claim 1, wherein the distal ends of said second set of optic fibers surrounds said first set of optic fibers and said second section of said inner face surrounds said first second of said inner face.

3. A fiber optic probe as recited in claim 2, further comprising means to transmit light to said window block through one of said first and second sets of optic fibers and means to receive light transmitted from said window block through the other one of said first and second sets of optic fibers.

4. A fiber optic probe as recited in claim 1, wherein said first and second sections of said inner face are separated by a boundary between said first and second sections and wherein a separator is provided between said first and second portions of the distal end of said fiber optic cable aligned with said boundary.

5. A fiber optic probe as recited in claim 1, further comprising means to transmit light to said window block through one of said first and second sets of optic fibers and means to receive light transmitted from said window block through the other one of said first and second sets of optic fibers.

6. A fiber optic probe comprising a fiber optic cable having optic fibers terminating in a distal end of said fiber optic cable, said optic fibers being segregated into a first set having distal ends in an outer portion of said distal end of said fiber optic cable and a second set having distal ends segregated in a central portion of said distal end of said fiber optic cable, a transparent window block having an inner face in the form of a truncated cone positioned adjacent to said distal end of said fiber optic cable, said inner face of said window defining a central section positioned opposite the distal ends of the optic fibers in said second set and a conical section surrounding said central section positioned opposite the distal ends of said optic fibers in said first set, said window block having an outer face opposite said inner face arranged to transmit light transmitted through said window block from one of said first and second sets of said optic fibers.

7. A fiber optic probe as recited in claim 6, wherein light is transmitted to said window block through said second set of optic fibers and wherein the angle of said conical section of said inner face and said outer face are arranged so that light from said first set of fibers, refracted by said conical section of said inner face and specularly reflected from said outer face are directed outside the boundary of said central section of said inner face.

8. A fiber optic probe as recited in claim 6, wherein a separator is provided between said outer portion and said central portion of said distal end of said fiber optic cable.

9. A fiber optic probe as recited in claim 6, further comprising means to transmit light to said window block through one of said first and second sets of optic fibers and means to receive light transmitted from said window block through the other one of said first and second sets of optic fibers.

10. A window block for a fiber optic probe comprising a block of transparent material having an inner face formed in the shape of a truncated cone concentric about an axis of said window block and an outer face perpendicular to said axis of said window block.

11. A window block as recited in claim 10, having sidewalls extending between said inner face and said outer face shaped as a surface of revolution about said axis.

12. A window block as recited in claim 11, wherein said side walls are tapered from said outer face to said inner face.

* * * * *